(12) United States Patent
Oshlack et al.

(10) Patent No.: US 6,572,885 B2
(45) Date of Patent: Jun. 3, 2003

(54) ORALLY ADMINISTRABLE OPIOID FORMULATIONS HAVING EXTENDED DURATION OF EFFECT

(75) Inventors: Benjamin Oshlack, New York, NY (US); Mark Chasin, Manalapan, NJ (US)

(73) Assignee: Euro-Celtique, S.A., Luxembourg (LU)

( * ) Notice: Subject to any disclaimer, the term of this patent is extended or adjusted under 35 U.S.C. 154(b) by 0 days.

(21) Appl. No.: 09/891,882

(22) Filed: Jun. 26, 2001

(65) Prior Publication Data

US 2002/0081333 A1 Jun. 27, 2002

Related U.S. Application Data

(63) Continuation of application No. 09/390,719, filed on Sep. 7, 1999, now Pat. No. 6,294,195, which is a continuation of application No. 08/508,246, filed on Jul. 27, 1995, now Pat. No. 5,968,551, which is a continuation of application No. 08/133,503, filed on Oct. 7, 1993, now abandoned, which is a continuation-in-part of application No. 08/086,248, filed on Jul. 1, 1993, now abandoned, and a continuation-in-part of application No. 08/081,618, filed on Jun. 23, 1993, now Pat. No. 5,472,712, which is a continuation-in-part of application No. 07/814,111, filed on Dec. 24, 1991, now Pat. No. 5,273,760, said application No. 08/086,248, is a continuation-in-part of application No. 07/814,111, said application No. 08/133,503, is a continuation-in-part of application No. 08/097,558, filed on Jul. 27, 1993, now Pat. No. 5,580,578, which is a continuation-in-part of application No. 07/826,084, filed on Jan. 27, 1992, now Pat. No. 5,286,493.

(51) Int. Cl.[7] .............................. A61K 9/14; A61K 9/16; A61K 9/48; A61K 9/52; A61K 9/54

(52) U.S. Cl. .................. 424/456; 424/457; 424/458; 424/461; 424/462; 424/489; 424/490; 424/494; 424/497

(58) Field of Search ................................ 424/456, 457, 424/458, 460, 462, 461, 484, 489, 490, 497, 494

(56) References Cited

U.S. PATENT DOCUMENTS

| 3,634,584 A | 1/1972 | Poole ........................... 424/21 |
| 3,845,770 A | 11/1974 | Theeuwes et al. ........... 128/260 |
| 3,870,790 A | 3/1975 | Lowey et al. ................. 424/19 |

(List continued on next page.)

FOREIGN PATENT DOCUMENTS

| AU | 9047732 | 7/1990 |
| AU | 9341654 | 2/1995 |
| CA | 2082573 | 11/1992 |

(List continued on next page.)

OTHER PUBLICATIONS

Advertisement: Roxanol SR, ©1988 Roxane Laboratories, Inc.

R. Kaiko and T. Hunt, "Comparison of the Pharmacokinetic Profiles of Two Oral Controlled–Release Morphine Formulations in Healthy Young Adults", Clin. Thera., vol. 13, No. 4, 1991.

R. West and C. Maccarrone, "Single Dose Pharmacokinetics of a New Oral Sustained–Release Morphine Formulation, Kapanol@ Capsules", Abstracts—7th World Congress on Pain, Aug. 26, 1993, Abstracts 997–1001.

(List continued on next page.)

*Primary Examiner*—James M. Spear
(74) *Attorney, Agent, or Firm*—Davidson, Davidson & Kappel, LLC (57) ABSTRACT

Sustained release oral solid dosage forms of opioid analgesics are provided as multiparticulate systems which are bioavailable and which provide effective blood levels of the opioid analgesic for at least about 24 hours. A unit dose of the opioid analgesic contains a plurality of substrates including the opioid analgesic in sustained release form. The substrates have a diameter from about 0.1 mm to about 3 mm.

22 Claims, 1 Drawing Sheet

U.S. PATENT DOCUMENTS

| | | | |
|---|---|---|---|
| 3,916,899 A | 11/1975 | Theeuwes et al. | 128/145.8 |
| 4,377,568 A | 3/1983 | Chopra | 424/31 |
| 4,385,078 A | 5/1983 | Onda et al. | 427/3 |
| 4,389,393 A | 6/1983 | Schor et al. | 424/19 |
| 4,483,847 A | 11/1984 | Augart | 424/22 |
| 4,520,172 A | 5/1985 | Lehmann et al. | 525/369 |
| 4,548,990 A | 10/1985 | Mueller et al. | 525/123 |
| 4,557,925 A | 12/1985 | Lindahl et al. | 424/19 |
| 4,600,645 A | 7/1986 | Ghebre-Sellassie et al. | 428/403 |
| 4,708,874 A | 11/1987 | De Haan et al. | 424/470 |
| 4,728,513 A | 3/1988 | Ventouras | 424/461 |
| 4,797,410 A | 1/1989 | El-Fakahany | 514/356 |
| 4,806,337 A | 2/1989 | Snipes et al. | 71/65 |
| 4,828,836 A | 5/1989 | Elger et al. | 424/419 |
| 4,834,984 A | 5/1989 | Goldie et al. | 424/488 |
| 4,834,985 A | 5/1989 | Elger et al. | 424/488 |
| 4,844,907 A | 7/1989 | Elger et al. | 424/488 |
| 4,844,909 A | 7/1989 | Goldie et al. | 424/480 |
| 4,861,598 A | 8/1989 | Oshlack | 424/468 |
| 4,970,075 A | 11/1990 | Oshlack | 424/451 |
| 4,983,730 A | 1/1991 | Domeshek et al. | 536/69 |
| 4,990,341 A | 2/1991 | Goldie et al. | 424/484 |
| 5,007,790 A * | 4/1991 | Shell | 424/451 |
| 5,024,842 A | 6/1991 | Edgren et al. | 424/473 |
| 5,071,646 A | 12/1991 | Malkowska et al. | 424/497 |
| 5,122,384 A | 6/1992 | Paradissis et al. | 424/451 |
| 5,133,974 A * | 7/1992 | Paradissis et al. | 424/480 |
| 5,169,645 A | 12/1992 | Shukla et al. | 424/499 |
| 5,178,868 A | 1/1993 | Malmqvist-Granlund et al. | 424/490 |
| 5,202,128 A | 4/1993 | Morella et al. | 424/469 |
| 5,266,331 A | 11/1993 | Oshlack et al. | 424/468 |
| 5,273,760 A * | 12/1993 | Oshlack et al. | 424/480 |
| 5,283,065 A | 2/1994 | Doyon et al. | 424/467 |
| 5,286,493 A * | 2/1994 | Oshlack et al. | 424/468 |
| 5,321,012 A | 6/1994 | Mayer et al. | 514/25 |
| 5,330,766 A | 7/1994 | Morella et al. | 424/490 |
| 5,378,474 A | 1/1995 | Morella et al. | 424/469 |
| 5,411,745 A | 5/1995 | Oshlack et al. | 424/456 |
| 5,456,923 A | 10/1995 | Nakamichi et al. | 424/489 |
| 5,460,826 A | 10/1995 | Merrill et al. | 424/470 |
| 5,472,712 A | 12/1995 | Oshlack et al. | 424/480 |
| 5,500,227 A | 3/1996 | Oshlack et al. | 424/476 |
| 5,508,042 A | 4/1996 | Oshlack et al. | 42/468 |
| 5,520,931 A | 5/1996 | Persson et al. | 424/473 |
| 5,549,912 A | 8/1996 | Oshlack et al. | 424/468 |
| 5,580,578 A | 12/1996 | Oshlack et al. | 424/468 |
| 5,601,842 A | 2/1997 | Bartholomaeus | 424/464 |
| 5,614,218 A | 3/1997 | Olsson et al. | 424/456 |
| 5,672,360 A | 9/1997 | Sackler et al. | 424/490 |
| 5,968,551 A * | 10/1999 | Oshlack et al. | 424/456 |
| 6,103,261 A | 8/2000 | Chasin et al. | 424/459 |
| 6,143,322 A | 11/2000 | Sackler et al. | 424/459 |

FOREIGN PATENT DOCUMENTS

| | | | |
|---|---|---|---|
| CA | 2131350 | 9/1994 | A61K/31/135 |
| EP | 0097523 | 1/1984 | A61K/9/26 |
| EP | 0108218 | 5/1984 | A61K/9/22 |
| EP | 0147780 | 7/1985 | A61K/9/32 |
| EP | 0235986 | 9/1987 | A61K/9/16 |
| EP | 0253104 | 1/1988 | A61K/9/00 |
| EP | 0271193 | 6/1988 | A61K/31/485 |
| EP | 377518 | 7/1990 | |
| EP | 0377518 | 7/1990 | A61K/9/52 |
| EP | 0388954 | 9/1990 | A61K/9/14 |
| EP | 0415693 | 3/1991 | A61K/37/02 |
| EP | 0532348 | 3/1993 | A61K/31/135 |
| EP | 0533297 | 3/1993 | A61K/9/16 |
| EP | 0534628 | 3/1993 | A61K/31/485 |
| EP | 0535841 | 4/1993 | A61K/31/485 |
| EP | 0546676 | 6/1993 | A61K/31/60 |
| EP | 0548448 | 6/1993 | A61K/9/50 |
| EP | 0580860 | 2/1994 | A61K/9/14 |
| EP | 0636370 | 6/1994 | A61K/31/485 |
| EP | 0609961 | 8/1994 | A61K/31/485 |
| EP | 0665010 | 8/1995 | A61K/9/26 |
| EP | 377518 | 2/1996 | |
| GB | 2053681 | 2/1981 | A61K/9/22 |
| GB | 2178313 | 2/1987 | A61K/9/14 |
| JP | 6330427 | 2/1988 | A61K/47/00 |
| JP | 03114 | 1/1991 | A61K/9/28 |
| JP | 4312524 | 11/1992 | A61K/9/52 |
| JP | 4321621 | 11/1992 | A61K/9/52 |
| TW | 177293 | 1/1992 | |
| WO | 0377518 | 7/1990 | A61K/9/52 |
| WO | WO 9201446 | 2/1992 | A61K/9/50 |
| WO | WO 9206679 | 4/1992 | A61K/9/16 |
| WO | WO 9304675 | 3/1993 | A61K/31/16 |
| WO | WO 9310765 | 6/1993 | A61K/9/22 |
| WO | 9310765 | 6/1993 | A61K/9/22 |
| WO | WO 9318753 | 9/1993 | A61K/9/16 |
| WO | 9403160 | 2/1994 | A61K/9/32 |
| WO | WO 9403161 | 2/1994 | A61K/9/52 |
| WO | 9403161 | 2/1994 | A61K/9/52 |
| WO | 9405262 | 3/1994 | A61K/9/16 |
| WO | 9422431 | 10/1994 | A61K/9/20 |
| WO | 9600066 | 1/1996 | A61K/31/485 |
| WO | 9601629 | 1/1996 | A61K/31/485 |
| WO | 9614058 | 3/1996 | A61K/9/14 |

OTHER PUBLICATIONS

S. Bloomfield, et al., "Analgesic efficacy and potency of two oral controlled–release morphine preparations", Clin. Pharmacol. Ther., vol. 53, No. 4, pp. 469–478, ©1993.

Advertisement: MS Contin®, ©1986, 1987, The Purdue Frederick Company.

Abraham Sunshine, et al., "Analgesic oral efficacy of tramadol hydrochloride in postoperative pain", *Clin. Pharmacol. Ther.*, Jun. 1992, pp. 740–746.

E. Beubler, "Medikamentose Schmerztherapie: Kriterien, Moglichkeiten, Risken", *Therapiewoche Osterreich*, 7, 2 (1992), pp. 90–96, with English translation.

Geoffrey K. Gourlay, Ph.D., et al., "Influence of a high–fat meal on the absorption of morphine from oral solutions", *Clin. Pharmacol. Ther.*, Oct. 1989, pp. 463–468.

Robert Kaiko, et al., "A Single–Dose Study Of The Effect Of Food Ingestion And Timing Of Dose Administration On The Pharmacokinetic Profile Of 30–MG Sustained–Release Morphine Sulfate Tablets", *Current Therapeutic Research*, vol. 47, No. 5, May 1990, pp. 869–878.

Geoffrey K. Gourlay, Ph.D., "The Reproducibility of Bioavailability of Oral Morphine from Solution Under Fed and Fasted Conditions", *Journal of Pain and Symptom Management*, vol. 6, No. 7, Oct. 1991, pp. 431–436.

Robert F. Kaiko, et al., "Controlled–Release Morphine Bioavailability (MS Contin Tablets) in the Presence and Absence of Food", *The Hospice Journal*, vol. 6(4) 1990, pp. 17–30.

N. Yokokawa, et al., "Relationship between plasma concentration of morphine and analgesic effectiveness", *Postgrad Med J*, (1991) 67 (Suppl. 2) pp. 550–554.

Physicians Desk Reference 1994, 48th Edition, pp. 1821–1824.

Bloomfield, et al., Clin. Pharmacaol. Ther., vol. 53, No. 4, pp. 469–478, 1993.

Advertisement: MS Contin® ©1986, 1987 The Purdue Frederick Company.

R. West et al. World Congress on Pain Abstracts 997–1001, Aug. 26, 1993.

Advertisement: Roxanol SR., ©1988 Floxane Labs, Inc.

R. Kaiko and T. Hunt, Clin. Thera. vol. 13, No. 4, pp. 484–488, 1991.

R.K. Portenoy, et al., "A Randomized, Double–Blind, Double–Dummy, Crossover Study Comparing the Pharmacokinetics and Pharmacodynamics of Kapanol® Capsules Given Every 24 hours and Every 12 hours with MS Contin® Tablets Given Every 12 Hours in the Management of Patients with Moderate to Severe Chronic Pain".

R.F. Kaiko, "The Pre–and Postoperative Use of Controlled–Release Morphine (MS Contin Tablets): A Review of the Published Literature", Medical Department, The Purdue Frederick Company, Royal Society of Medical Services, International Congress, Symposium Services, No. 149, pp. 147–160 (1989).

H.F. Slowey et al., "Effect of Premedication with Controlled–Release Oral Morphine on Postoperative Pain", Anaesthesia, 1985, vol. 40, pp. 438–440.

MS Contin—Frequency of Daily Dosing, Jan.–Nov. 1990.

Abstracts from the Twelfth Annual Congress of the Oncology Nursing Society, May 1987.

J. Lapin et al., "Cancer Pain Management with a Controlled Release Oral Morphine Preparation", Journ. of Pain and Symptom Manag., v 4(3), pp. 146–151, 1989.

J. Lapin et al., "Guidelines for use of Controlled Release Oral Morphine in Cancer Pain Management", Cancer Nursing, v 12 (4), pp. 202–208, 1989.

Certain documents regarding Institutional Review Board Approval for the Faulding–sponsored study.

Investigator Agreements between the study organizers and certain of the principal investigators.

A protocol for a clinical study entitled "A Randomized, Double–Blind, Parallel–Group Study comparing the Efficacy and Safety of Kapanol® to Ms. Contin® in the Management of Patients with Moderate to Severe Cancer Pain" ("the Protocol"). The date of the Protocol is indicated as Feb. 10, 1992 and it bears CDD No. 14556. The sponsor of the study is indicated to be Faulding Pharmaceuticals, an Australian company.

Certain Patient Diary Cards, Drug Disposition Records, Case Report Forms and a listing which apparently correlates patient randomization number with the treatment or dosing regimen assigned to each patient.

Patient consent forms, apparently for four study participants.

MS Contin—Frequency of Daily Dosing (NDTI)—Jun., 1991–May, 1992.

MS Contin—Frequency of Daily Dosing—Jan.–Nov., 1990.

Maccarrone C. et al; Single Dose Pharmacokinetics of Kapanol™, a New Oral Sustained–Release Morphine Formulation; Clinical Drug Investigation 1994:7 (5): 262–274.

West RJ. Maccarrone C. Single dose pharmacokinetics of a new sustained release morphine formulation, Kapanol™ capsules. (Abstract 997) International Association for the Study of Pain, 7th World Congress on Pain. Paris, Aug. 22–27, 1993 (Data on file. Glaxo Australia, F.H. Faulding).

Gourlay GK, Plummer JL, Cherry DA, et al. A comparison of Kapanol™ (A new sustained release morphine formulation), MST Continus® and morphine solution in cancer patients: pharmacokinetic aspects. (Abstract 998) International Association for the Study of Pain, 7th World Congress on Pain. Paris, Aug. 22–27, 1993 (Data on file, Glaxo Australia, F.H. Faulding).

Cherry DA, Gourlay GK, Plummer JL, et al. A comparison of Kapanol™ (a new sustained release morphine formulation), MST Continus® and morphine solution in cancer patients: morphine profiles and renal function. (Abstract 999) International Association for the Study of Pain, 7th World Congress on Pain, Paris, Aug. 22–27, 1993.

Plummer JL, Cherry DA, Gourlay GK, et al. A comparison of Kapanol™ (a new sustained release morphine formulation) MST Continus® and morphine solution in cancer patients: pharmacodynamic aspects. (Abstract 1000) International Association for the Study of Pain, 7th World Congress on Pain, Paris, Aug. 22–27, 1993 (Data on file, Glaxo Australia, F.H. Faulding).

Toner G, Cramond T, Bishop J, et al. Randomized double blind, phase III crossover study of a new sustained–release oral morphine formulation, Kapanol™ capsules, (Abstract 1001) International Association for the Study of Pain, 7th World Congress on Pain, Paris, Aug. 22–27, 1993 (Data on file, Glaxo Australia, F.H. Faulding).

European Journal of Cancer, Once A Day (i.e. 24 Hourly) Kapanol™, A New Sustained Release Morphine Formulation, in the Treatment of Cancer Pain: Morphine Metabolite Profiles; Part A General Topics 1995;31 (S5) Suppl:S184 Abs 884, European Conference on Clinical Oncology and Cancer Nursing, Paris, Oct. 29–Nov. 2 1995.

European Journal of Cancer; Once A Day (i.e. 24 Hourly) Kapanol™, A New Sustained Release Morphine Formulation, In The Treatment of Cancer Pain: Pharmacokinetic Aspects; Part A General Topics 1995:31 (S5) Suppl: S187 Abs 897 European Conference on Clinical Oncology and Cancer Nursing, Paris, Oct. 29–Nov. 2, 1995.

European Journal of Cancer; Kadian™/Kapanol™—A Once Daily Morphine Fomulation; Part A General Topics 1995;31 (S5) Suppl: S182 Abs 873 European Conference on Clinical Oncology and Cancer Nursing, Paris, Oct. 29–Nov. 2, 1995.

Gourlay et al., Proceeding of the 7th World Congress on Pain; A comparison of Kapanol (a New Sustained–Release Morphine Formulation), MST Continus, and Morphine Solution in Cancer Patients: Pharmacokinetic Aspects of Morphine and Morphine Metabolites Progress in Pain Research and Management vol. 2 pp. 631–643.

Kaiko R.F.; Clinical Protocol and Role of Controlled Release Morphine in the Surgical Patient; Anesthesiology and Pain Management 1991 pp. 193–212.

MS Contin—Frequency of Daily Dosing (NDTI)—Jun. 1991—May, 1992.

* cited by examiner though the dissolution of drug substance from its carrier, the dis-
ORALLY ADMINISTRABLE OPIOID FORMULATIONS HAVING EXTENDED DURATION OF EFFECT This application is a continuation of U.S. application Ser. No. 09/390,719, filed Sep. 7, 1999 now U.S. Pat. No. 6,294,195, pending, which is a continuation of U.S. application Ser. No. 08/508,246, filed Jul. 27, 1995, now U.S. Pat. No. 5,968,551, which is a continuation of U.S. application Ser. No. 08/133,503, filed Oct. 7, 1993, abandoned, which is a continuation-in-part of both U.S. patent application Ser. No. 08/081,618 filed Jun. 23, 1993, now U.S. Pat. No. 5,472,712, and of U.S. patent application Ser. No. 08/086,248 filed Jul. 1, 1993, abandoned, both of which are continuations-in-part of U.S. patent application Ser. No. 07/814,111, filed Dec. 24, 1991, now U.S. Pat. No. 5,273,760. U.S. application Ser. No. 08/133,503 is also a continuation-in-part of U.S. patent application Ser. No. 08/097,558 filed Jul. 27, 1993, now U.S. Pat. No. 5,580,578, which in turn is a continuation-in-part of U.S. Ser. No. 07/826,084 filed Jan. 27, 1992, now U.S. Pat. No. 5,286,493.

BACKGROUND OF THE INVENTION

The present invention relates to bioavailable sustained-release pharmaceutical formulations of analgesic drugs, in particular opioid analgesics, which provide an extended duration of effect when orally administered.

It is known in the pharmaceutical art to prepare compositions which provide for controlled (slow) release of pharmacologically active substances contained in the compositions after oral administration to humans and animals. Such slow release compositions are used to delay absorption of a medicament until it has reached certain portions of the alimentary tract. Such sustained-release of a medicament in the alimentary tract further maintains a desired concentration of said medicament in the blood stream for a longer duration than would occur if conventional rapid release dosage forms are administered.

Slow release formulations known in the art include specially coated pellets, coated tablets and capsules wherein the slow release of the active medicament is brought about through selective breakdown of the coating of the preparation or through compounding with a special matrix to affect the release of a drug. Some slow release formulations provide for related sequential release of a single dose of an active compound at predetermined periods after administration.

It is the intent of all sustained-release preparations to provide a longer period of pharmacologic response after the administration of the drug and is ordinarily experienced after the administration of the rapid release dosage forms. Such longer periods of response provide for many inherent therapeutic benefits that are not achieved with corresponding short acting, immediate release preparations. This is especially true in the treatment of cancer patients or other patients in need of treatment for the alleviation of moderate to severe pain, where blood levels of an opioid analgesic medicament must be maintained at a therapeutically effective level to provide pain relief. Unless conventional rapid acting drug therapy is carefully administered at frequent intervals to maintain effective steady state blood levels of the drug, peaks and valleys in the blood level of the active drug occur because of the rapid absorption, systemic excretion of the compound and through metabolic inactivation, thereby producing special problems in maintenance of analgesic efficacy.

The prior art teaching of the preparation and use of compositions providing the sustained-release of an active compound from a carrier is basically concerned with the release of the active substance into the physiologic fluid of the alimentary tract. However, it is generally recognized that the mere presence of an active substance in the gastrointestinal fluids does not, by itself, insure bioavailability.

In order to be absorbed, the active drug substance must be in solution. The time required for a given proportion of an active substance from a unit dosage form is determined as the proportion of the amount of active drug substance released from a unit dosage form over a specified time base by a test method conducted under standardized conditions. The physiologic fluids of the gastrointestinal tract are the media for determining dissolution time. The present state of the art recognizes many satisfactory test procedures to measure dissolution time for pharmaceutical compositions, and these test procedures are described in official compendia world wide.

Although there are many diverse factors which influence the dissolution of drug substance from its carrier, the dissolution time determined for a pharmacologically active substance from the specific composition is relatively constant and reproducible. Among the different factors affecting the dissolution time are the surface area of the drug substance presented to the dissolution solvent medium, the pH of the solution, the solubility of the substance in the specific solvent medium, and the driving forces of the saturation concentration of dissolved materials in the solvent medium. Thus, the dissolution concentration of an active drug substance is dynamically modified in its steady state as components are removed from the dissolution medium through absorption across the tissue site. Under physiologic conditions, the saturation level of the dissolved materials is replenished from the dosage form reserve to maintain a relatively uniform and constant dissolution concentration in the solvent medium providing for a steady state absorption.

The transport across a tissue absorption site of the gastrointestinal tract is influenced by the Donnan osmotic equilibrium forces on both sides of the membrane since the direction of the driving force is the difference between the concentrations of active substance on either side of the membrane, i.e., the amount dissolved in the gastrointestinal fluids and the amount present in the blood. Since the blood levels are constantly being modified by dilution, circulatory changes, tissue storage, metabolic conversion and systemic excretion, the flow of active materials is directed from the gastrointestinal tract into the blood stream.

Notwithstanding the diverse factors influencing both dissolution and absorption of a drug substance, a strong correlation has been established between the in-vitro dissolution time determined for a dosage form and (in-vivo) bioavailability. The dissolution time and the bioavailability determined for a composition are two of the most significant fundamental characteristics for consideration when evaluating sustained-release compositions.

It has previously been known in the art that sustained-release compositions of opioids or salts thereof could be prepared in a suitable matrix. For example, in U.S. Pat. Nos. 4,990,341 and 4,844,909 (Goldie, et al.), both assigned to the assignee of the present invention, describes hydromorphone compositions wherein the dissolution rate in vitro of the dosage form, when measured by the USP Paddle or Basket Method at 100 rpm in 900 ml aqueous buffer (pH between 1.6 and 7.2) at 37° C., is between 12.5 and 42.5% (by wt) hydromorphone released after 1 hour, between 25 and 55% (by wt) released after 2 hours, between 45 and 75% (by wt) released after 4 hours and between 55 and 85% (by wt) released after 6 hours, the in vitro release rate being independent of pH between pH 1.6 and 7.2 and chosen such that the peak plasma level of hydromorphone obtained in vivo occurs between 2 and 4 hours after administration of the dosage form. At least 12 hours of pain relief is obtained with the hydromorphone formulations.

Once-a-day orally administrable dosage forms have previously been developed in the art and are commercially available. However, currently, there are no orally administered opioid formulations commercially available which provide an extended duration of effect, e.g., greater than about 12 hours. Examples of commercially available once-a-day dosage forms include Dilacor® XR (diltiazem hydroxide, extended-release capsules, available from Rhone-Poulenc Rorer), Thorazine® Spanule® (chlorpromazine HCl, extended-release capsules, available from SmithKline Beecham), Theo-24® (theophylline, extended-release capsules, available from Searle), TheoX® (theophylline, extended-release tablets, available from Carnrick), Theo-dur® (theophylline, extended-release tablets, available from Key), Theo-Sav® (theophylline, extended-release tablets, available from Sauage), Uniphyl® Unicontin® (theophylline, extended-release tablets, available from Purdue Frederick), T-Phyl® Unicontin® (theophylline, extended-release tablets, available from Purdue Frederick), Tenuate Dospan® (diethylpropion HCl, extended-release tablets, available from Marion Merrill Dow), Tepanil® Ten-Tab® (diethylpropion HCl, extended-release tablets, available from 3M Riker), Desoxyn® Gradumet® (phenmetrazine HCl, extended-release tablets, available from Abbott), Dexedrine® Spanule® (dextroamphetamine, extended-release capsules, available from SmithKline Beecham), Compazine® Spanule® (prochlorperazine maleate, extended-release capsules, available from SmithKline Beecham), Indocin® SR (indomethacin, extended-release capsules, available from Merck), Betachron® (propranolol HCl, extended-release capsules, available from Inwood), Inderal® LA (propranolol HCl, extended-release capsules, available from Wyeth-Ayerst), Inderide® LA (propranolol HCl and hydrochlorothiazide, extended-release capsules from Wyeth-Ayerst), Procardia XL® (nifedipine, extended-release tablets, available from Pfizer), Mestinon® Timespan® (pyridostigmine Br, extended-release tablets, available from ICN), Temaril® Spanule® (trimeprazine tartrate, extended-release capsules, available from Herbert), AL-R® 6 (chlorpheniramine maleate, extended-release capsules, available from Saron), Chlor-Trimeton® Allergy Repetabs® (chlorpheniramine maleate, extended-release tablets, available from Schering-Plough), Adipost® (phendimetrazine tartrate, extended-release capsules, available from Ascher), Bontril® Slow-Release (phendimetrazine tartrate, extended-release capsules, available from Carnrick), Melfiat®-105 Unicelles® (phendimetrazine tartrate, extended-release capsules, available from Solway), Prelu-2® (phendimetrazine tartrate, extended-release capsules, available from Boehringer Ingelheim), PT 105® (phendimetrazine tartrate, extended-release capsules, available from Legere), Wehless®-105 Timecelles (phendimetrazine tartrate, extended-release capsules, available from Hauck), Preludin® Endurets® (phenmetrazine HCl, extended-release tablets, available from Boehringer Ingelheim), Caffedrine (caffeine, extended-release capsules, available from Thompson), Diamox® Sequels® (acetazolamide, extended-release capsules, available from Storz), Verelan® (verapamil HCl, extended-release capsules cont. pellets, available from Wyeth-Ayerst), Calan® SR Caplets® (verapamil HCl, extended-release tablets, available from Searle), Isoptin® SR (verapamil HCl, extended-release tablets, available from Knoll), Verapamil HCl Tablets (verapamil HCl, extended-release tablets, available from GoldLine), and Artane® Sequels® (trihexyphenidyl HCl, extended-release capsules, available from Lederle).

There is a need in the art to develop drug formulations which provide a duration of effect lasting longer than twelve hours such as a drug that may be administered to a patient only once a day. Many of the oral opioid analgesic formulations that are currently available in the market must be administered every four to six hours daily with a selected few formulated for less frequent 12 hour dosing.

Morphine, which is considered to be the prototypic opioid analgesic, has been formulated into 12 hour controlled-release formulations (i.e., MS Contin® tablets, commercially available from Purdue Frederick Company).

An orally administrable opioid formulation which would provide an extended duration of effect would be highly desirable. Such an oral sustained-release formulation of an opioid analgesic, would provide effective steady-state blood levels (e.g., plasma levels) of the drug when orally administered such that a duration of effect greater than 12 hours, and more preferably, of about 24 hours or more, which formulation is bioavailable as well.

OBJECTS AND SUMMARY OF THE INVENTION

It is accordingly an object of the present invention to provide an orally administered pharmaceutical dosage form of an opioid analgesic that is suitable for once-a-day administration.

Another object of the present invention is to provide a sustained-release products which provides effective steady-state blood levels in a human patient for greater than 12 hours, preferably at least 24 hours, which products are bioavailable.

Still another object of the present invention is to provide a method of treating a patient with an orally administrable dosage form of an opioid analgesic which provides a desired analgesic effect for a period of time greater than 12 hours, preferably for at least 24 hours and which dosage form is bioavailable.

In accordance with the above objects and others which will be apparent from the further reading of the specification and of the appended claims, the present invention is related to the surprising discovery that in order to provide a 24 hour dosage form of an opioid analgesic, it is necessary to do so via a sustained multiparticulate system. More particularly, the present invention is related to the surprising discovery that while sustained-release tablets and sustained-release multiparticulate systems containing opioid analgesics may be prepared which provide an in-vitro dissolution indicative of a 24 hour formulation, only sustained-release multiparticulate systems of opioid analgesics are bioavailable. This is true even when the sustained-release tablets have an in-vitro dissolution profile which is virtually equivalent to that provided by the multiparticulate system.

More particularly, the present invention relates to a sustained-release oral analgesic dosage form for once-a-day administration, comprising a unit dose of a plurality of inert pharmaceutically acceptable substrates. The unit dose of the substrates comprises an analgesically effective amount of an opioid analgesic or a salt thereof. Each of said substrates having a diameter from about 0.1 mm to about 3 mm. The unit dose is bioavailable and provides effective blood levels of the opioid analgesic for at least about 24 hours. The unit dose of the substrates may be, for example, contained within a hard gelatin capsule for oral administration.

In certain preferred embodiments of the present invention, each of the substrates has a diameter from about 0.5 mm to about 2 mm (narrower range).

The present invention is further related to a bioavailable sustained-release opioid analgesic dosage form for once-a-day oral administration, comprising inert pharmaceutically acceptable beads having a diameter from about 0.1 mm to about 3 mm coated with an analgesically effective amount of an opioid analgesic or a salt thereof. The beads further comprise a sustained-release overcoat comprising an effective amount of a hydrophobic material selected from the group consisting of (i) an acrylic polymer such as copolymers of acrylic and methacrylic acid; (ii) an alkylcellulose such as ethylcellulose; (iii) other commonly used retardant coatings such as shellac, zein, and hydrophobic waxy-type products, such as hydrogenated castor oil or hydrogenated vegetable oil, or (iv) mixtures of any of groups (i)–(iii) to provide a sustained-release of said opioid analgesic in aqueous solutions for at least about 24 hours.

The present invention is further related to a method for obtaining a bioavailable sustained-release opioid analgesic dosage form for once-a-day oral administration, comprising preparing a plurality of substrates comprising a unit dose of an oral analgesic in a sustained-release form, each of which substrates having a diameter from about 0.1 mm to about 3 mm. The substrates are manufactured to provide an in-vitro dissolution indicative of a once-a-day product.

The term "bioavailable" is defined for the purposes of the present invention as the total amount of a drug substance that is absorbed to be available to provide the desired therapeutic effect after administration of a unit dosage form, as compared to the known reference drug product, as commonly determined and accepted by Governmental Regulatory Agencies, such as the United States FDA.

The term "bioavailability" is defined for purposes of the present invention as the extent to which the drug (e.g., opioid analgesic) is absorbed from the unit dosage forms and becomes available at the site of drug action.

The terms "sustained release" and "extended duration" are defined for purposes of the present invention as the release of the drug (e.g., opioid analgesic) at such a rate that blood (e.g., plasma) levels are maintained within the therapeutic range but below toxic levels over a period of time greater than 12 hours, more preferably for about 24 hours, or longer.

The term "substrate" is defined for the purposes of the present invention as spheroids, beads, microspheres, seeds, pellets, ion-exchange resin beads, and other multi-particulate systems comprising the drug(s), which have a diameter from about 0.1 mm to about 3 mm, preferably between 0.5 mm and 2.0 mm.

The term "unit dose" is defined for purposes of the present invention as the total amount of substrates needed to administer a desired dose of drug (e.g., opioid analgesic) to a patient.

The sustained-release substrates of the present invention permit release of the opioid (or salt) over a sustained period of time in an aqueous medium. The term "aqueous medium" is defined for purposes of the present invention as any pharmaceutically acceptable dissolution medium, gastric fluid and/or intestinal fluid.

BRIEF DESCRIPTION OF THE DRAWING

The following drawing is illustrative of an embodiment of the invention and is not meant to limit the scope of the invention as encompassed by the claims.

DETAILED DESCRIPTION

The multiparticulate systems of the present invention may incorporate one or more compounds known as opioid analgesics. Opioid analgesic compounds which may be used in the present invention include alfentanil, allylprodine, alphaprodine, anileridine, benzylmorphine, bezitramide, buprenorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levallorphan, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene, sufentanil, tramadol, tilidine, salts thereof, mixtures of any of the foregoing, mixed mu-agonists/antagonists, mu-antagonist combinations, and the like.

In certain preferred embodiments, the opioid analgesic is selected from morphine, codeine, hydromorphone, hydrocodone, oxycodone, dihydrocodeine, dihydromorphine, oxymorphone, or mixtures thereof.

In one preferred embodiment the sustained-release opioid oral dosage form of the present invention includes hydromorphone as the therapeutically active ingredient in an amount from about 4 to about 64 mg hydromorphone hydrochloride. Alternatively, the dosage form may contain molar equivalent amounts of other hydromorphone salts or of the hydromorphone base. In other preferred embodiments where the opioid analgesic is other than hydromorphone, the dosage form contains an appropriate amount to provide a substantially equivalent therapeutic effect. For example, when the opioid analgesic comprises morphine, the sustained-release oral dosage forms of the present invention include form about 5 mg to about 800 mg morphine, by weight. When the opioid analgesic comprises oxycodone, the sustained-release oral dosage forms of the present invention include from about 5 mg to about 400 mg oxycodone.

The sustained-release dosage forms of the present invention generally achieve and maintain therapeutic levels substantially without significant increases in the intensity and/or degree of concurrent side effects, such as nausea, vomiting or drowsiness, which are often associated with high blood levels of opioid analgesics. There is also evidence to suggest that the use of the present dosage forms leads to a reduced risk of drug addiction. Furthermore, the sustained-release dosage forms of the present invention preferably release the opioid analgesic at a rate that is independent of pH, e.g., between pH 1.6 and 7.2. In other words, the dosage forms of the present invention avoid "dose dumping" upon oral administration.

In the present invention, the oral opioid analgesics have been formulated to provide for an increased duration of analgesic action allowing once-daily dosing. Surprisingly, these formulations, at comparable daily dosages of conventional immediate-release drug, are associated with a lower incidence in severity of adverse drug reactions and can also be administered at a lower daily dose than conventional oral medication while maintaining pain control.

The substrates of the present invention may further include one or more additional drugs which may or may not act synergistically with the opioid analgesics of the present invention. Examples of such additional drugs include non-steroidal anti-inflammatory agents, including ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid tolfenamic acid, diflurisal, flufenisal, piroxicam, sudoxicam or isoxicam, and the like. Other suitable additional drugs which may be included in the dosage forms of the present invention include acetaminophen, aspirin, and other non-opioid analgesics.

For example, if a second (non-opioid) drug is included in the formulation, such drug may be included in controlled release form or in immediate release form. The additional drug may be incorporated into the controlled release matrix along with the opioid; incorporated into the controlled release coating; incorporated as a separated controlled release layer or immediate release layer; or may be incorporated as a powder, granulation, etc., in a gelatin capsule with the substrates of the present invention.

The sustained-release preparations of the present invention may be used in conjunction with any multiparticulate system, such as beads, spheroids, microspheres, seeds, pellets, ion-exchange resin beads, and other multiparticulate systems in order to obtain a desired sustained-release of the therapeutically active agent. Beads, granules, spheroids, or pellets, etc., prepared in accordance with the present invention can be presented in a capsule or in any other suitable unit dosage form.

When the substrates of the present invention are inert pharmaceutical beads, the inert pharmaceutical beads may be from about 8 mesh to about 50 mesh. In certain preferred embodiments, the beads are, e.g., nu pariel 18/20 beads.

In certain preferred embodiments of the present invention, the sustained-release opioid dosage forms comprise a plurality of substrates comprising the active ingredient, which substrates are coated with a sustained-release coating. The coating formulations of the present invention should be capable of producing a strong, continuous film that is smooth and elegant, capable of supporting pigments and other coating additives, non-toxic, inert, and tack-free.

In order to obtain a sustained-release of the opioid sufficient to provide an analgesic effect for the extended durations set forth in the present invention, the substrate comprising the therapeutically active agent may be coated with a sufficient amount of hydrophobic material to obtain a weight gain level from about 2 to about 30 percent, although the overcoat may be greater depending upon the physical properties of the particular opioid analgesic compound utilized and the desired release rate, among other things.

The solvent which is used for the hydrophobic material may be any pharmaceutically acceptable solvent, including water, methanol, ethanol, methylene chloride and mixtures thereof. It is preferable however, that the coatings be based upon aqueous dispersions of the hydrophobic material.

In certain preferred embodiments of the present invention, the hydrophobic polymer comprising the sustained-release coating is a pharmaceutically acceptable acrylic polymer, including but not limited to acrylic acid and methacrylic acid copolymers, methacrylic acid copolymers, methyl methacrylate copolymers, ethoxyethyl methacrylates, cynaoethyl methacrylate, methyl methacrylate, copolymers, methacrylic acid copolymers, methyl methacrylate copolymers, methyl methacrylate copolymers, methyl methacrylate copolymers, methacrylic acid copolymer, aminoalkyl methacrylate copolymer, methacrylic acid copolymers, methyl methacrylate copolymers, poly(acrylic acid), poly(methacrylic acid, methacrylic acid alkylamide copolymer, poly(methyl methacrylate), poly(methacrylic acid) (anhydride), methyl methacrylate, polymethacrylat, methyl methacrylate copolymer, poly(methyl methacrylate), poly (methyl methacrylate) copolymer, polyacrylamide, aminoalkyl methacrylate copolymer, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic coating is an acrylic resin lacquers used in the form of an aqueous dispersion, such as that which is commercially available from Rohm Pharma under the Tradename Eudragit®. In further preferred embodiments, the acrylic coating comprises a mixture of two acrylic resin lacquers commercially available from Rohm Pharma under the Tradenames Eudragit® RL 30 D and Eudragit® RS 30 D, respectively. Eudragit® RL 30 D and Eudragit® RS 30 D are copolymers of acrylic and methacrylic esters with a low content of quaternary ammonium groups, the molar ratio of ammonium groups to the remaining neutral (meth)acrylic esters being 1:20 in Eudragit® RL 30 D and 1:40 in Eudragit® RS 30 D. The mean molecular weight is about 150,000. The code designations RL (high permeability) and RS (low permeability) refer to the permeability properties of these agents. Eudragit® RL/RS mixtures are insoluble in water and in digestive fluids. However, coatings formed from the same are swellable and permeable in aqueous solutions and digestive fluids.

The Eudragit® RL/RS dispersions of the present invention may be mixed together in any desired ratio in order to ultimately obtain a sustained-release formulation having a desirable dissolution profile. Desirable sustained-release formulations may be obtained, for instance, from a retardant coating derived from 100% Eudragit® RL, 50% Eudragit® RL and 50% Eudragit® RS, and 10% Eudragit® RL:Eudragit® 90% RS. Of course, one skilled in the art will recognize that other acrylic polymers may also be used, such as, for example, Eudragit® L.

In other preferred embodiments, the hydrophobic polymer which may be used for coating the substrates of the present invention is a hydrophobic cellulosic material such as ethylcellulose. Those skilled in the art will appreciate that other cellulosic polymers, including other alkyl cellulosic polymers, may be substituted for part or all of the ethylcellulose included in the hydrophobic polymer coatings of the present invention.

One commercially-available aqueous dispersion of ethylcellulose is Aquacoat® (FMC Corp., Philadelphia, Penn., U.S.A.). Aquacoat® is prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, it is necessary to intimately mix the Aquacoat® with a suitable plasticizer prior to use.

Another aqueous dispersion of ethylcellulose is commercially available as Surelease® (Colorcon, Inc., West Point, Penn., U.S.A.). This product is prepared by incorporating plasticizer into the dispersion during the manufacturing process. A hot melt of a polymer, plasticizer (dibutyl sebacate), and stabilizer (oleic acid) is prepared as a homogeneous mixture, which is then diluted with an alkaline solution to obtain an aqueous dispersion which can be applied directly onto substrates.

In embodiments of the present invention where the coating comprises an aqueous dispersion of a hydrophobic polymer, the inclusion of an effective amount of a plasticizer in the aqueous dispersion of hydrophobic polymer will further improve the physical properties of the film. For example, because ethylcellulose has a relatively high glass transition temperature and does not form flexible films under normal coating conditions, it is necessary to plasticize the ethylcellulose before using the same as a coating material. Generally, the amount of plasticizer included in a coating solution is based on the concentration of the film-former, e.g., most often from about 1 to about 50 percent by weight of the film-former. Concentration of the plasticizer, however, can only be properly determined after careful experimentation with the particular coating solution and method of application.

Examples of suitable plasticizers for ethylcellulose include water insoluble plasticizers such as dibutyl sebacate, diethyl phthalate, triethyl citrate, tibutyl citrate, and triacetin, although it is possible that other water-insoluble plasticizers (such as acetylated monoglycerides, phthalate esters, castor oil, etc.) may be used. Triethyl citrate is especially preferred.

Examples of suitable plasticizers for the acrylic polymers of the present invention include citric acid esters such as triethyl citrate NF XVI, tributyl citrate, dibutyl phthalate, and possibly 1,2-propylene glycol, polyethylene glycols, propylene glycol, diethyl phthalate, castor oil, and triacetin, although it is possible that other water-insoluble plasticizers (such as acetylated monoglycerides, phthalate esters, castor oil, etc.) may be used. Triethyl citrate is especially preferred.

The sustained-release profile of the formulations of the invention can be altered, for example, by varying the thickness of the hydrophobic coating, changing the particular hydrophobic material used, or altering the relative amounts of, e.g., different acrylic resin lacquers, altering the manner in which the plasticizer is added (e.g., when the sustained-release coating is derived from an aqueous dispersion of hydrophobic polymer), by varying the amount of plasticizer relative to hydrophobic polymer, by the inclusion of additional ingredients or excipients, by altering the method of manufacture, etc.

Sustained-release spheroids or beads, coated with a therapeutically active agent are prepared, e.g. by dissolving the opioid analgesic in water and then spraying the solution onto a substrate, for example, nu pariel 18/20 beads, using a Wurster insert. Optionally, additional ingredients are also added prior to coating the beads in order to assist the hydromorphone binding to the substrates, and/or to color the solution, etc. For example, a product which includes hydroxypropyl methylcellulose, etc. with or without colorant may be added to the solution and the solution mixed (e.g., for about 1 hour) prior to application of the same onto the beads. The resultant coated substrate, in this example beads, may then be optionally overcoated with a barrier agent, to separate the therapeutically active agent from the hydrophobic sustained-release coating. An example of a suitable barrier agent is one which comprises hydroxypropyl methylcellulose. However, any film-former known in the art may be used. It is preferred that the barrier agent does not affect the dissolution rate of the final product.

The hydromorphone, HPMC protected (optional) beads may then be overcoated with hydrophobic polymer, preferably with an effective amount of plasticizer.

The coating solutions of the present invention may contain, in addition to the film-former, plasticizer, and solvent system (i.e., water), a colorant to provide elegance and product distinction. Color may be added to the solution of the therapeutically active agent instead, or in addition to the aqueous dispersion of hydrophobic polymer.

The plasticized aqueous dispersion of hydrophobic polymer may be applied onto the substrate comprising the therapeutically active agent by spraying using any suitable spray equipment known in the art. In a preferred method, a Wurster fluidized-bed system is used in which an air jet, injected from underneath, fluidizes the core material and effects drying while the acrylic polymer coating is sprayed on. A sufficient amount of the aqueous dispersion of hydrophobic polymer to obtain a predetermined sustained-release of said therapeutically active agent when said coated substrate is exposed to aqueous solutions, e.g. gastric fluid, is preferably applied, taking into account the physically characteristics of the therapeutically active agent, the manner of incorporation of the plasticizer, etc. After coating with the hydrophobic polymer, a further overcoat of a film-former, such as Opadry®, is optionally applied to the beads. This overcoat is provided, if at all, in order to substantially reduce agglomeration of the beads.

Next, the coated beads are cured in order to obtain a stabilized release rate of the therapeutically active agent.

When the coating comprises an aqueous dispersion of ethylcellulose, the coated substrate is preferably subjected to curing at a temperature greater than the glass transition temperature of the coating solution (i.e., ethylcellulose) and at a relative humidity from about 60% to about 100%, until the curing endpoint is reached, e.g., about 60° C. and a relative humidity from about 60% to about 100% for a time period from about 48 to about 72 hours.

In preferred embodiments of the present invention directed to the acrylic coating, a stabilized product is obtained by subjecting the coated substrate to oven curing at a temperature above the Tg of the plasticized acrylic polymer for the required time period, the optimum values for temperature and time for the particular formulation being determined experimentally. In certain embodiments of the present invention, the stabilized product is obtained via an oven curing conducted at a temperature of about 45° C. for a time period from about 24 to about 48 hours or longer.

The release of the therapeutically active agent from the sustained-release formulation of the present invention can be further influenced, i.e., adjusted to a desired rate, by the addition of one or more release-modifying agents, or by providing one or more passageways through the coating. The ratio of hydrophobic polymer to water soluble material is determined by, among other factors, the release rate required and the solubility characteristics of the materials selected.

The release-modifying agents which function as pore-formers may be organic or inorganic, and include materials that can be dissolved, extracted or leached from the coating in the environment of use. The pore-formers may comprise one or more hydrophilic polymers such as hydroxypropylmethylcellulose.

The sustained-release coatings of the present invention can also include erosion-promoting agents such as starch and gums.

The sustained-release coatings of the present invention can also include materials useful for making microporous lamina in the environment of use, such as polycarbonates comprised of linear polyesters of carbonic acid in which carbonate groups reoccur in the polymer chain.

The release-modifying agent may also comprise a semipermeable polymer.

In certain preferred embodiments, the release-modifying agent is selected from hydroxypropylmethylcellulose, lactose, metal stearates, and mixtures of any of the foregoing.

The sustained-release coatings of the present invention may also include an exit means comprising at least one passageway, orifice, or the like. The passageway may be formed by such methods as those disclosed in U.S. Pat. Nos. 3,845,770; 3,916,889; 4,063,064; and 4,088,864 (all of which are hereby incorporated by reference). The passageway can have any shape such as round, triangular, square, elliptical, irregular, etc.

In other embodiments of the present invention, the present invention may utilize a multiparticulate sustained-release matrix. Suitable materials for inclusion in a sustained-release matrix are (a) Hydrophilic polymers, such as gums, cellulose ethers, acrylic resins and protein derived materials. Of these polymers, the cellulose ethers, especially hydroxyalkylcelluloses and carboxyalkylcelluloses, are preferred. The oral dosage form may contain between 1% and 80% (by weight) of at least one hydrophilic or hydrophobic polymer.

(b) Digestible, long chain ($C_8C_{50}$, especially $C_{12}$–$C_{40}$), substituted or unsubstituted hydrocarbons, such as fatty acids, fatty alcohols, glyceryl esters of fatty acids, mineral and vegetable oils and waxes. Hydrocarbons having a melting point of between 25° and 90° C. are preferred. Of these long chain hydrocarbon materials, fatty (aliphatic) alcohols are preferred. The oral dosage form may contain up to 60% (by weight) of at least one digestible, long chain hydrocarbon.

(c) Polyalkylene glycols. The oral dosage form may contain up to 60% (by weight) of at least one polyalkylene glycol.

For example, a suitable matrix may be one which comprises at least one water soluble hydroxyalkyl cellulose, at least one $C_{12}$–$C_{36}$, preferably $C_{14}$–$C_{22}$, aliphatic alcohol and, optionally, at least one polyalkylene glycol. The at least one hydroxyalkyl cellulose is preferably a hydroxy ($C_1$ to $C_6$) alkyl cellulose, such as hydroxypropylcellulose, hydroxypropylmethylcellulose and, especially, hydroxyethyl cellulose. The amount of the at least one hydroxyalkyl cellulose in the present oral dosage form will be determined, inter alia, by the precise rate of opioid release required. The at least one aliphatic alcohol may be, for example, lauryl alcohol, myristyl alcohol or stearyl alcohol. In certain preferred embodiments, the at least one aliphatic alcohol is cetyl alcohol or cetostearyl alcohol. The amount of the at least one aliphatic alcohol in the present oral dosage form will be determined, as above, by the precise rate of opioid release required. It will also depend on whether at least one polyalkylene glycol is present in or absent from the oral dosage form. In the absence of at least one polyalkylene glycol, the oral dosage form preferably contains between 20% and 50% (by wt) of the at least one aliphatic alcohol. When at least one polyalkylene glycol is present in the oral dosage form, then the combined weight of the at least one aliphatic alcohol and the at least one polyalkylene glycol preferably constitutes between 20% and 50% (by wt) of the total dosage.

In one embodiment, the ratio of, e.g., at least one hydroxyalkyl cellulose or acrylic resin to at least one aliphatic alcohol/ polyalkylene glycol determines, to a considerable extent, the release rate of the opioid from the formulation. A ratio of the at least one hydroxyalkyl cellulose to at least one aliphatic alcohol/ polyalkylene glycol of between 1:2 and 1:4 is preferred, with a ratio of between 1:3 and 1:4 being particularly preferred.

At least one polyalkylene glycol may be, for example, polypropylene glycol or, preferably, polyethylene glycol. The number average molecular weight of the at least one polyalkylene glycol is preferred between 1000 and 15000 especially between 1500 and 12000.

Another suitable sustained-release matrix would comprise an alkylcellulose (especially ethyl cellulose), a $C_{12}$ to $C_{36}$ aliphatic alcohol and, optionally, a polyalkylene glycol.

In addition to the above ingredients, a sustained-release matrix may also contain suitable quantities of other materials, e.g., diluents, lubricants, binders, granulating aids, colorants, flavorants and glidants that are conventional in the pharmaceutical art.

In order to facilitate the preparation of a solid, sustained-release oral dosage form according to this invention there is provided, in a further aspect of the present invention, a process for the preparation of a solid, sustained-release oral dosage form according to the present invention comprising incorporating opioids or a salt thereof in a sustained-release matrix. Incorporation in the matrix may be effected, for example, by (a) forming granules comprising at least one water soluble hydroxyalkyl cellulose and opioid or an opioid salt, (b) mixing the hydroxyalkyl cellulose containing granules with at least one $C_{12}$–$C_{36}$ aliphatic alcohol, and (c) optionally, compressing and shaping the granules. Preferably, the granules are formed by wet granulating the hydroxyalkyl cellulose/opioid with water. In a particularly preferred embodiment of this process, the amount of water added during the wet granulation step is preferably between 1.5 and 5 times, especially between 1.75 and 3.5 times, the dry weight of the opioid.

In yet other alternative embodiments, a spheronizing agent, together with the active ingredient can be spheronized to form spheroids. Microcrystalline cellulose is preferred. A suitable microcrystalline cellulose is, for example, the material sold as Avicel PH 101 (Trade Mark, FMC Corporation). In such embodiments, in addition to the active ingredient and spheronizing agent, the spheroids may also contain a binder. Suitable binders, such as low viscosity, water soluble polymers, will be well known to those skilled in the pharmaceutical art. However, water soluble hydroxy lower alkyl cellulose, such as hydroxy propyl cellulose, are preferred. Additionally (or alternatively) the spheroids may contain a water insoluble polymer, especially an acrylic polymer, an acrylic copolymer, such as a methacrylic acid-ethyl acrylate copolymer, or ethyl cellulose. In such embodiments, the sustained-release coating will generally include a water insoluble material such as (a) a wax, either alone or in admixture with a fatty alcohol; or (b) shellac or zein.

The substrates of the present invention may also be prepared via a melt pellitization technique. In such circumstance, the opioid in finely divided form is combined with a binder (also in particulate form) and other optional inert ingredients, and thereafter the mixture is pelletized, e.g., by mechanically working the mixture in a high shear mixer to form the pellets (granules, spheres). Thereafter, the pellets (granules, spheres) may be sieved in order to obtain pellets of the requisite size. The binder material is preferably in particulate form and has a melting point above about 40° C. Suitable binder substances include, for example, hydrogenated castor oil, hydrogenated vegetable oil, other hydrogenated fats, fatty alcohols, fatty acid esters, fatty acid glycerides, and the like.

In certain embodiments of the present invention, an effective amount of opioid in immediate release form is included in the unit dose comprising the substrates of the present invention. The immediate release form of the opioid is included in an amount which is effective to shorten the time to maximum concentration of the opioid in the blood (e.g., plasma), such that the $T_{max}$ is shortened to a time of, e.g., from about 2 to about 4 hours. This causes the blood concentration curve to have an early peak rather than the substantially flattened curves currently recommended by those skilled in the art. It has been discovered that by including such an effective amount of immediate release opioid in the unit dose, the experience of relatively higher levels of pain in patients is significantly reduced. In such embodiments, an effective amount of the opioid in immediate release form may be coated onto the substrates of the present invention. For example, where the extended release opioid from the formulation is due to a controlled release coating, the immediate release layer would be overcoated on top of the controlled release coating. on the other hand, the immediate release layer may be coated onto the surface of substrates wherein the opioid is incorporated in a controlled release matrix. Where a plurality of the sustained release substrates comprising an effective unit dose of the opioid are incorporated into a hard gelatin capsule, the immediate release portion of the opioid dose may be incorporated into the gelatin capsule via inclusion of the sufficient amount of immediate release opioid as a powder or granulate within the capsule. Alternatively, the gelatin capsule itself may be coated with an immediate release layer of the opioid. One skilled in the art would recognize still other alternative manners of incorporating the immediate release opioid portion into the unit dose. Such alternatives are deemed to be encompassed by the appended claims.

DETAILED DESCRIPTION OF THE PREFERRED EMBODIMENTS

The following examples illustrate various aspects of the present invention. They are not to be construed to limit the claims in any manner whatsoever.

EXAMPLE 1

Sustained-Release Beads with Ethylcellulose Coating

In Example 1, morphine sulfate sustained-release beads with a 5% w/w sustained-release of ethylcellulose were prepared, including 3% of HPMC as a pore-former in the coating.

Morphine sulfate beads are first manufactured using a rotor processing technique. The formula of the morphine sulfate bead to which the sustained-release coating is applied is set forth in Table 1 below:

TABLE 1

| Ingredient | Amt/Unit (mg) | Percent (%) |
|---|---|---|
| Morphine Sulfate Powder | 30 mg | 14.3% |
| Lactose Hydrous Impalpable | 42.5 mg | 20.2% |
| PVP | 2.5 mg | 1.2% |
| Sugar Beads 18/20 | 125 mg | 59.4% |
| Purified Water | qs | — |
| Opadry ® Red YS-1-1841 | 10.5 mg | 4.9% |
| Total | 210.5 mg | 100.0% |

The morphine sulphate beads were then overcoated with a sustained-release coating. The formula for the sustained-release coating is set forth in Table 2 below:

TABLE 2

| Ingredient | Amt/Unit (mg) | Percent (%) |
|---|---|---|
| Morphine Sulfate Base Beads | 210.5 mg | 89.7% |
| Aquacoat ECD 30 (solids) | 10.2 mg | 4.3% |
| Methocel E5 Premium | 0.3 mg | 0.1% |
| Triethyl Citrate | 2.1 mg | 0.9% |
| Purified Water | qs | — |
| Opadry ® Red YS-1-1841 | 11.7 mg | 5.0% |
| Purified Water | qs | — |
| Total | 234.8 mg | 100.0% |

The sustained-release coating was manufactured as follows:

The pore former Methocel E5 Premium (HPMC), is dispersed and dissolved in purified water to yield a 2% w/w solution. An Aquacoat dispersion is plasticized with triethyl citrate for approximately 30 minutes. After 30 minutes the HPMC dispersion is mixed into the plasticized Aquacoat dispersion, and blended for an additional 15–30 minutes. A load of the morphine sulfate beads is charged into a Uniglatt Wurster Insert equipped with a 1.2 mm fluid nozzle. The beads are then filmcoated with the Aquacoat/HPMC dispersion (in a ratio of 93:7) to a weight gain of 5%.

After completion of the coating process, the coated beads are taken from the Wurster Insert to a tray and then cured in a chamber at a temperature of 60° C. and humidity of 80% RH for 72 hours. Upon completion of the curing process, the beads are dried to a LOD of 4% or less. The beads are then given a final overcoating of Opadry® Red YS-1-1841 (15% w/w solution) with the use of the Wurster Insert. The coated morphine sulfate beads are then filled into hard gelatin capsules.

Dissolution testing were conducted on the finished products via USP Apparatus II-(Paddle Method). The capsules were placed into 700 ml of simulated gastric fluid (without enzymes) for the first hour at 100 rpm and 37° C., and then placed into 900 ml of simulated gastric fluid (without enzymes) after the first hour. The results are set forth in Table 3 below:

TABLE 3

| Time | Percent Morphine Sulfate Dissolved |
|---|---|
| 1 hour | 18.4% |
| 2 hours | 28.4% |
| 4 hours | 46.7% |
| 8 hours | 73.1% |
| 12 hours | 86.0% |
| 18 hours | 95.0% |
| 24 hours | 99.0% |

The dissolution testing as set forth in Table 3 indicates that 100% of the morphine sulfate dissolved after 12 hours.

EXAMPLE 2

Sustained-Release Beads with Acrylic Polymer Coating

In example 2, morphine sulfate sustained-release beads with a 5% w/w sustained-release Eudragit RS were prepared, including a 10% immediate release morphine sulfate overcoat.

Morphine sulfate beads are first manufactured using a rotor processing technique. The formula of the morphine sulfate bead to which the sustained-release coating is applied is set forth in Table 4 below:

TABLE 4

| Ingredient | Amt/Unit (mg) | Percent (%) |
|---|---|---|
| Morphine Sulfate Powder | 30 mg | 14.3% |
| Lactose Hydrous Impalpable | 42.5 mg | 20.2% |
| PVP | 2.5 mg | 1.2% |
| Sugar Beads 18/20 | 125 mg | 59.4% |
| Purified Water | qs mg | — |
| Opadry Red YS-1-1841 | 10.5 mg | 4.9% |
| Total | 210.5 mg | 100.0% |

A sustained-release coating was then applied to the morphine sulfate beads. The formula for the functional coating is set forth in Table 5 below:

TABLE 5

| Ingredient | Amt/Unit (mg) | Percent (%) |
|---|---|---|
| Morphine Base Beads | 189.45 mg | 86.7% |
| Retardant Coating | | |
| Eudragit RS 30D | 9.5 mg | 4.3% |
| Triethyl Citrate | 1.9 mg | 0.9% |
| Talc | 3.8 mg | 1.7% |
| Purified Water | qs | — |
| Overcoat | | |
| Morphine Sulfate Powder | 3.0 mg | 1.4% |
| Opadry Red YS-1-1841 | 10.8 mg | 5.0% |
| Purified Water | qs | — |
| Total | 218.45 mg | 100.0% |

The sustained-release coating is manufactured as follows:

The Eudragit RS 30D is plasticized with triethyl citrate and talc for approximately 30 minutes. A load of the morphine sulfate beads is charged into a Wurster Insert of a Glatt equipped with a 1.2 mm spray nozzle and the beads are coated to a weight gain of 5%. The final protective Opadry dispersion overcoat is then applied in the Wurster Insert. Upon completion the beads are cured for two days in a dry oven of 45° C. The cured beads were then filled into gelatin capsules at a 30 mg strength.

Dissolution testing were conducted on the gelatin capsules via U.S.P. Apparatus II (Paddle Method). The capsules were placed into 700 ml of simulated gastric fluid (without enzymes) for the first hour at 100 rpm and 37° C., and then placed into 900 ml of simulated gastric fluid (without enzymes) after the first hour. The results of the percent of morphine sulfate dissolved in relation to time, are set forth in Table 6 below:

TABLE 6

| Time | Percent Morphine Sulfate Dissolved |
|---|---|
| 1 hour | 11.9% |
| 2 hours | 15.4% |
| 4 hours | 28.1% |
| 8 hours | 58.3% |
| 12 hours | 79.2% |
| 18 hours | 92.0% |
| 24 hours | 96.6% |

The dissolution testing as set forth in Table 6 indicates that 96.6% of the morphine sulfate dissolved after 24 hours.

EXAMPLE 3

High Load Sustained-Release Beads with Acrylic Polymer Coating

In certain circumstances, patients require higher doses of morphine sulfate. However, if the low load beads of Examples 1 and 2 were filled to a weight equivalent to 60 mg or more, the capsules would be relatively large, and difficult to swallow. Therefore, in Example 3, beads with a higher loading of morphine sulfate were produced with the use of the powder layering technique in the Glatt Rotor Processor. The formulation of the high load beads, as well as a comparison of the high load beads with the low load beads of Examples 1 and 2, are set forth in Table 7 below:

TABLE 7

| Ingredient | High Load Bead mg/unit | Percent (%) | Low Load Bead (Examples 1 & 2) mg/unit | Percent (%) |
|---|---|---|---|---|
| Morphine Sulfate Powder | 30.0 mg | 63.3% | 30.0 mg | 14.3% |
| Lactose | 6.0 mg | 12.7% | 42.5 mg | 20.2% |
| Povidone C-30 | 1.25 mg | 2.6% | 2.5 mg | 1.2% |
| Sugar Beads | 7.75 mg | 16.4% | 125.0 mg | 59.4% |
| Opadry | 2.37 mg | 5.0% | 10.5 mg | 4.9% |
| Purified Water | qs | — | qs | — |
| Total | 47.37 mg | 100.0% | 210.5 mg | 100.0% |

Since high load beads of Example 3 are different from the low load beads of Examples 1 and 2, the sustained-release coating a different acrylic polymer (i.e., Eudragit® RL, which is more soluble than Eudragit® RS) is utilized, as well as extra HPMC protective coat between the Eudragit layer and the morphine immediate release layer to further enhance stability. The formula of the sustained-release coating of Example 3 is set forth in Table 8 below:

TABLE 8

| Ingredient | Amt/Unit (mg) | Percent (%) |
| --- | --- | --- |
| Morphine (high load) base beads | 42.63 mg | 78.8% |
| Retardant Coating | | |
| Eudragit RS 30D | 2.1 mg | 3.9% |
| Eudragit RL 30D | 0.05 mg | 0.1% |
| Triethyl Citrate | 0.45 mg | 0.8% |
| Talc | 0.85 mg | 1.6% |
| Overcoatings | | |
| Opadry Blue YS-1-10542A | 2.45 mg | 4.5% |
| Purified Water | qs | — |
| Morphine Sulfate Powder | 3.0 mg | 5.5% |
| Opadry Blue YS-1-10542A | 2.55 mg | 4.8% |
| Purified Water | qs | — |
| Total | 54.08 mg | 100.0% |

The sustained-release and the immediate release coatings were applied in the manner described in Example 2. The cured beads were then filled into gelating capsules at a strength of 30 mg.

The capsules were then subjected to dissolution testing applying the method described in Example 1. The results of dissolution testing is set forth in Table 9 below:

TABLE 9

| Time | Percent Morphine Sulfate Dissolved |
| --- | --- |
| 1 hour | 11.7% |
| 2 hours | 12.1% |
| 4 hours | 22.0% |
| 8 hours | 45.3% |
| 12 hours | 63.7% |
| 18 hours | 81.8% |
| 24 hours | 92.5% |

The dissolution testing as set forth in Table 9 indicates that 92.5% of the morphine sulfate dissolved after 24 hours.

EXAMPLE 4

Sustained-Release Tablets

Controlled release morphine sulfate tablets were developed with an in-vitro dissolution profile that would be suitable for once-a-day administration. The formula of the morphine sulfate tablets is set forth in Table 10 below.

TABLE 10

| Ingredient | Amt/Unit (mg) | Percent (%) |
| --- | --- | --- |
| Morphine Sulfate | 60.0 mg | 40.0% |
| Lactose | 36.1 mg | 24.1% |
| Povidone | 6.0 mg | 4.0% |
| Eudragit RS 30D (solids) | 12.0 mg | 8.0% |
| Triacetin | 1.4 mg | 0.9% |
| Cetostearyl alcohol | 30.0 mg | 20.0% |
| Talc | 3.0 mg | 2.0% |
| Magnesium stearate | 1.5 mg | 1.0% |
| Total | 150.0 mg | 100.0% |

These tablets are manufactured in the following manner:

The morphine sulfate, lactose and povidone were added and mixed in fluid bed granulator. The triacetin, a plasticizer was mixed into the Eudragit RS 30D dispersion for about 30 minutes, and then was sprayed onto the powders using a 1.2 mm nozzle in the fluid bed. Once the spraying is completed, the granulate is screened. The cetostearyl alcohol is then melted and mixed into the granulation in a standard mixing bowl. The granulate is then cooled, screened and lubricated with talc and magnesium stearate. Tablets were then compressed at a weight of 150 mg.

Dissolution testing of these morphine sulfate tablets was then conducted using the method described in Example 1. The results of the dissolution testing of these tablets is set forth in Table 11 below:

TABLE 11

| Time | Percent Morphine Sulfate Dissolved |
| --- | --- |
| 1 hour | 20.9% |
| 2 hours | 29.3% |
| 4 hours | 40.8% |
| 8 hours | 59.9% |
| 12 hours | 69.7% |
| 18 hours | 82.9% |
| 24 hours | 90.5% |

The results of dissolution of the morphine sulfate tablets as set forth in Table 11 shows that 90.5% of the morphine sulfate dissolved in 24 hours.

Figure 1:
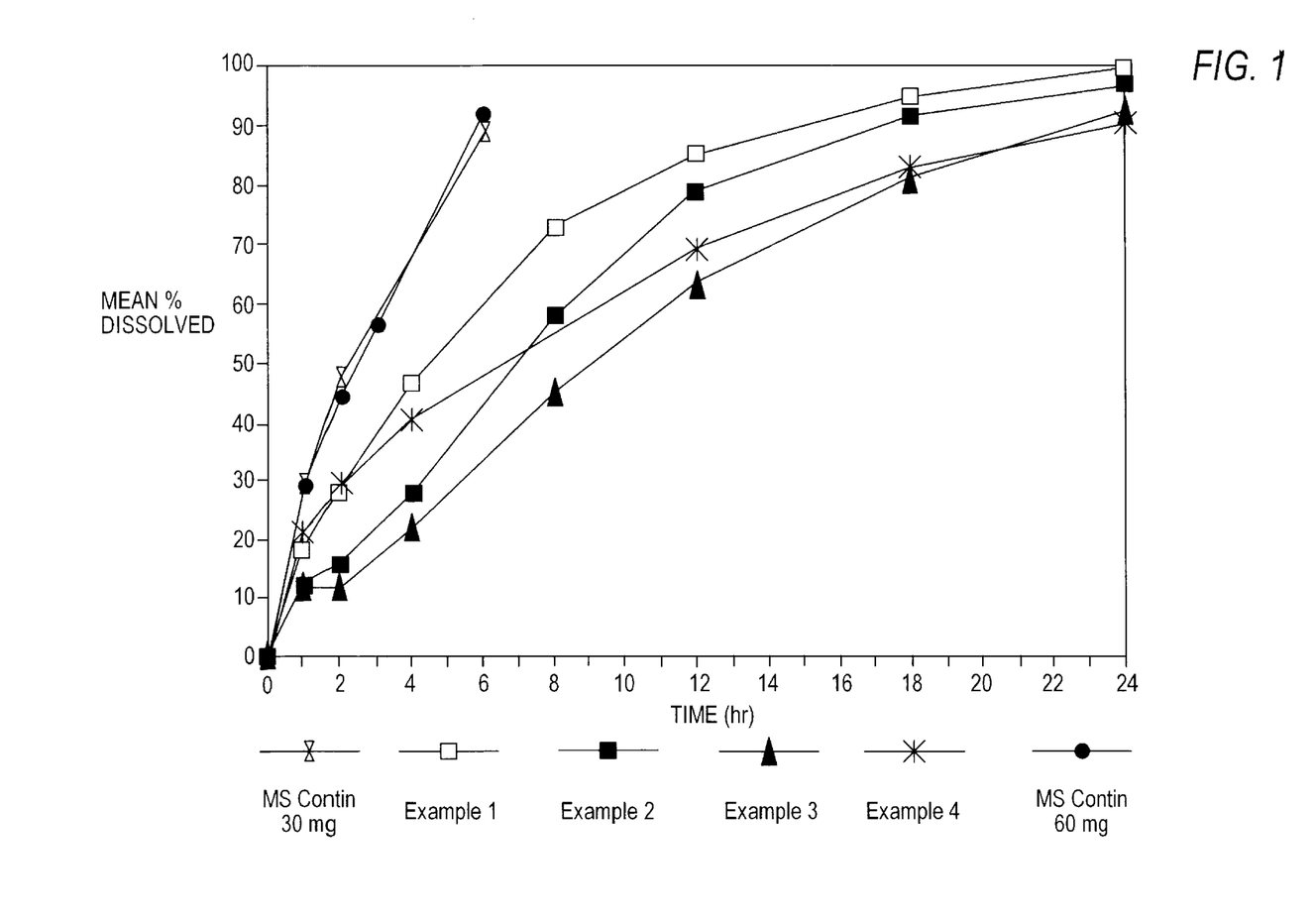
FIG. 1 is a graphical representation of the formulation dissolution obtained for Examples 1–4.

Examples 1, 2, 3 and 4 were plotted on a dissolution graph (see FIG. 1) and it can be observed that the dissolution of the morphine sulfate tablets of Example 4 are approximately the same as the three bead examples. The release rate of the tablets of Example 4 lies with the dissolution of the bead products (Examples 1–3). For reference purposes, the dissolution of MS Contin® 30 mg and 60 mg tablets were also plotted on FIG. 1. MS Contin® tablets are well known morphine sustained-release tablets that are commercially available from the Purdue Frederick Company for twice-a-day administration.

EXAMPLE 5

In-Vivo Bioavailability Studies

The bead products of Examples 1, 2 and 3 were then studied in separate human bioavailability studies at a dose of 30 mg. Each study also used a 30 mg strength MS Contin® as a reference in a cross-over design. The 60 mg tablet of Example 4 was compared to MS Contin® 60 mg as a reference in a cross-over study. The results of all four bioavailability studies are set forth in Tables 12–15 below. In Table 16, the in-vivo results of Example 4 are set forth with the results adjusted to a 30 mg strength. In each of Tables 12–16, $C_{max}$ is expressed in ng/ml; $T_{max}$ is expressed in hours; $W_{50}$ represents the peak width at half height in hours; and AUC represents the area under the curve (O to infinity), expressed in ng-hr/ml.

TABLE 12

| | Beads - Example 1 | | | | |
| --- | --- | --- | --- | --- | --- |
| | $C_{max}$ | $T_{max}$ | W50 | AUC | % Bioavail. |
| MS Contin ® 30 mg Tablets | 13 | 2.3 | 5 | 103 | (100) |
| Experimental Bead Formulation | 5.9 | 5.6 | 11.5 | 101 | 98 |

TABLE 13

Beads - Example 2

|  | $C_{max}$ | $T_{max}$ | W50 | AUC | % Bioavail. |
|---|---|---|---|---|---|
| MS Contin ® 30 mg Tablets | 13 | 2.2 | 5 | 99 | (100) |
| Experimental Bead Formulation | 5.4 | 5.9 | 17 | 107 | 108 |

TABLE 14

Beads - Example 3

|  | $C_{max}$ | $T_{max}$ | W50 | AUC | % Bioavail. |
|---|---|---|---|---|---|
| MS Contin ® 30 mg Tablets | 11.8 | 2.8 | 5 | 114 | (100) |
| Experimental Bead Formulation | 3.8 | 10.1 | 47 | 125 | 110 |

TABLE 15

Tablets - Example 4

|  | $C_{max}$ | $T_{max}$ | W50 | AUC | % Bioavail. |
|---|---|---|---|---|---|
| MS Contin ® 60 mg Tablets | 18.2 | 2.7 | 5.56 | 195.6 | (100) |
| Experimental Tablet Formulation | 8.8 | 3.2 | 13.19 | 129.5 | 66 |

TABLE 16

Example 4 - Adjusted to 30 mg Strength

|  | $C_{max}$ | $T_{max}$ | W50 | AUC | % Bioavail. |
|---|---|---|---|---|---|
| MS Contin ® | 9.1 | 2.7 | 5.56 | 97.8 | (100) |
| Experimental Tablet Formulation | 4.4 | 3.2 | 13.19 | 64.8 | 66 |

From the bioavailability studies, it can be observed that all three of the bead products of Examples 1, 2 and 3 exhibit pharmacokinetic properties which would allow them to be suitable for once-a-day administration. In other words, the bead products of Examples 1–3 were all bioavailable (as determined by comparing the AUC of the bead product to the AUC of the reference standard, MS Contin®). However, the tablet products of Example 4 were surprisingly not bioavailable despite the reduction of the peak plasma concentration ($C_{max}$) and the lengthening of the time to reach peak plasma concentration ($T_{max}$) and W-50 and even though the dissolution studies show that the morphine sulfate was released from the tablet products in-vitro over the same time period as the bead products.

Therefore, it is surprising result that a bioavailable once-a-day product was only produced when the sustained release opioid was formulation as a multiparticulate system (in this instance beads) as opposed to the sustained release tablet formulation, which from all other indications would have been expected to have substantially identical bioavailability.

The examples provided above are not meant to be exclusive. Many other variations of the present invention would be obvious to those skilled in the art, and are contemplated to be within the scope of the appended claims.

What is claimed is:

1. An oral analgesic dosage form for once-a-day administration, comprising
   (a)(i) inert pharmaceutically acceptable beads having a diameter from about 0.1 mm to 3 mm (ii) morphine or a pharmaceutically acceptable salt thereof disposed about the beads, and (iii) hydrophobic sustained-release material disposed about the morphine or pharmaceutically acceptable salt thereof, and
   (b) morphine or a pharmaceutically acceptable salt thereof in immediate release form; said dosage form providing a therapeutic effect for about 24 hours or more after oral administration to a human patient.

2. The dosage form of claim 1, wherein said hydrophobic material comprises an acrylic polymer.

3. The dosage form of claim 2, which comprises from about 5 mg to about 800 mg morphine.

4. The dosage form of claim 1, wherein the sustained-release beads release said morphine or pharmaceutically acceptable salt thereof at a rate that is independent of pH between pH 1.6 and 7.2.

5. The dosage form of claim 4, wherein the hydrophobic sustained-release material consists essentially of one or more ammonio methacrylate copolymers.

6. The dosage form of claim 5, wherein said hydrophobic sustained-release material is applied onto said beads as an aqueous dispersion of said ammonio methacrylate copolymers, and said beads are cured in order to obtain a stabilized release rate of said morphine or pharmaceutically acceptable salt thereof.

7. The dosage form of claim 1, wherein said beads and said morphine in immediate release form are contained in a gelatin capsule.

8. The dosage form of claim 1, which releases said morphine or pharmaceutically acceptable salt thereof at a rate such that after oral administration to a human, blood plasma levels of said morphine are maintained within the therapeutic range for about 24 hours.

9. The dosage form of claim 1, which provides effective steady-state blood plasma levels of said morphine for at least about 24 hours.

10. The dosage form of claim 1, wherein said morphine in immediate release form is 10% of said dosage form.

11. The dosage form of claim 6, wherein said morphine in immediate release form is 10% of said dosage form, and said dosage form provides effective steady-state blood plasma levels of said morphine for at least about 24 hours.

12. An oral analgesic dosage form for once-a-day administration, comprising
   (a) sustained release substrates comprising morphine or a pharmaceutically acceptable salt thereof and a hydrophobic material, said substrates having a diameter from about 0.1 mm to about 3 mm; and
   (b) morphine or a pharmaceutically acceptable salt thereof in immediate release form; said dosage form providing a therapeutic effect for about 24 hours or more after oral administration to a human patient.

13. The dosage form of claim 12, which provides effective steady-state blood plasma levels of said morphine for at least about 24 hours.

14. The dosage form of claim 12, wherein said immediate release portion of said morphine or pharmaceutically acceptable salt thereof is 10% of said unit dosage form.

15. The dosage form of claim 12, wherein said sustained-release substrates comprise (i) inert pharmaceutically acceptable beads having a diameter from about 0.1 mm to 3 mm (ii) morphine or a pharmaceutically acceptable salt thereof disposed about the beads, and (iii) said hydrophobic material being selected from the group consisting of one or more ammonio methacrylate copolymers, a hydrophobic cellulosic material, and mixtures thereof, said sustained-release substrates releasing said morphine or pharmaceutically acceptable salt thereof at a rate that is independent of pH between pH 1.6 and 7.2.

16. The dosage form of claim 15, wherein said hydrophobic material consists of one or more ammonio methacrylate copolymers.

17. The dosage form of claim 12, wherein said sustained release substrates comprise pharmaceutically acceptable matrices comprising said morphine or pharmaceutically acceptable salt thereof and a hydrophobic material.

18. A method for preparing an oral analgesic dosage form comprising (i) preparing sustained-release morphine multiparticulates by coating inert pharmaceutically acceptable beads having a diameter from about 0.1 mm to about 3 mm with morphine or a pharmaceutically acceptable salt thereof and thereafter overcoating said morphine-coated beads with sustained-release coating comprising a hydrophobic material; and (ii) combining an effective amount of said sustained-release morphine multiparticulates with an effective amount of said morphine or pharmaceutically acceptable salt thereof in immediate release form to obtain a dosage form which, upon oral administration to a human patient, provides a therapeutic effect for about 24 hours.

19. A method for treating a patient for pain, the method comprising administering to a patient once-a-day an oral analgesic dosage form comprising (a)(i) inert pharmaceutically acceptable beads having a diameter from about 0.1 mm to about 3 mm, (ii) morphine or a pharmaceutically acceptable salt thereof disposed about the beads, and (iii) hydrophobic sustained-release material disposed about the morphine; and (b) morphine or a pharmaceutically acceptable salt thereof in immediate release form; said dosage form providing a therapeutic effect for about 24 hours or more after oral administration to a human patient.

20. A method for treating a patient for pain, the method comprising administering to a patient once-a-day an oral analgesic dosage form comprising (a) sustained release substrates comprising morphine or a pharmaceutically acceptable salt thereof and a hydrophobic material, said substrates having a diameter from about 0.1 mm to about 3 mm; and (b) morphine or a pharmaceutically acceptable salt thereof in immediate release form; said dosage form providing a therapeutic effect for about 24 hours or more after oral administration to a human patient.

21. An oral analgesic dosage form for once-a-day administration, comprising (a) a therapeutically effective amount of morphine or a pharmaceutically acceptable salt thereof;

(b) means for providing sustained release of a portion of said morphine or pharmaceutically acceptable salt thereof; and (c) means for providing immediate release of the remaining portion of said morphine or pharmaceutically acceptable salt thereof; said dosage form providing a therapeutic effect for about 24 hours or more after oral administration to a human patient.

22. A method for treating a patient for pain, the method comprising administering to a patient once-a-day an oral analgesic dosage form comprising:

(a) a therapeutically effective amount of morphine or a pharmaceutically acceptable salt thereof;

(b) means for providing sustained release of a portion of said morphine or said pharmaceutically acceptable salt thereof; and (c) means for providing immediate release of the remaining portion of said morphine or pharmaceutically acceptable salt thereof; said dosage form providing a therapeutic effect for about 24 hours or more after oral administration to a human patient.

* * * * *

UNITED STATES PATENT AND TRADEMARK OFFICE
CERTIFICATE OF CORRECTION

PATENT NO. : 6,572,885 B2  
APPLICATION NO. : 09/891882  
DATED : June 3, 2003  
INVENTOR(S) : Oshlack et al.

Page 1 of 1

It is certified that error appears in the above-identified patent and that said Letters Patent is hereby corrected as shown below:

On the Title page, please correct the assignee to read as follows:

(73) Assignee: Purdue Pharma L.P., Stamford, CT (US)

Signed and Sealed this

Twenty Second Day of April, 2008

JON W. DUDAS  
*Director of the United States Patent and Trademark Office*